United States Patent [19]

Petty et al.

[11] Patent Number: 5,357,441

[45] Date of Patent: Oct. 18, 1994

[54] MOISTURE CONTENT MEASURING APPARATUS AND METHOD

[75] Inventors: J. Scott Petty, Hanover; Christopher Ferguson, Framingham; Joseph R. Adamski, Sudbury, all of Mass.; Joseph E. Musil, Ely, Iowa

[73] Assignee: Raytheon Company, Lexington, Mass.

[21] Appl. No.: 29,854

[22] Filed: Mar. 11, 1994

[51] Int. Cl.⁵ .......................................... G08B 21/00
[52] U.S. Cl. ................................ 364/469; 340/604;
340/605; 340/583; 340/619; 250/573
[58] Field of Search ................ 364/469; 340/604, 601,
340/602, 605, 555, 556, 557; 73/293, 170 R,
171; 239/63, 64, 65; 250/227.11–227.32,
573–577; 137/392

[56] References Cited

U.S. PATENT DOCUMENTS

| Re. 31,023 | 9/1982 | Hall | 47/1 R |
|---|---|---|---|
| 3,771,548 | 11/1973 | Rauchwerger | 137/392 |
| 3,803,570 | 4/1974 | Barlow et al. | 340/235 |
| 4,445,788 | 5/1984 | Twersky et al. | 374/142 |
| 4,892,113 | 1/1990 | Fattahi | 137/78.3 |
| 5,005,005 | 4/1991 | Brossia et al. | 340/604 |
| 5,071,514 | 12/1991 | Francis | 162/259 |
| 5,239,203 | 8/1993 | Thorngren | 307/116 |

Primary Examiner—Envall, Jr. Roy N.
Assistant Examiner—Cameron H. Tousi
Attorney, Agent, or Firm—William R. Clark

[57] ABSTRACT

A moisture content measuring apparatus and method wherein a sensor station produces calibration data corresponding to measurements of light at two different wavelengths reflected from a material, and the calibration data is then transferred to a hand held computer. The moisture content of a sample of the material is measured and input to the hand held computer. The process is repeated after changing the wetness of the material, and the hand held computer creates a table correlating reflection data to moisture content. The table is transferred to the sensor station which then continuously generates signals representing moisture content in response to real time reflection data and the table. The cost effectiveness of the sensor stations readily facilitates the use of a dedicated sensor station at each of a plurality of conveyors carrying different materials to be combined into a composite of predetermined proportions by weight. Based on the real time moisture contents of each material, the respective flow rates are adjusted to compensate for moisture in order to produce the predetermined proportion.

17 Claims, 3 Drawing Sheets

MOISTURE CONTENT MEASURING APPARATUS AND METHOD

BACKGROUND OF THE INVENTION

This invention generally relates to moisture content measuring apparatus and method, and more particularly relates to a relatively inexpensive moisture content sensor station and the use of a plurality of such sensor stations to control an industrial process that is dependent on the moisture content of a plurality of different materials.

As is well known, knowledge of the moisture content of materials is desirable for many industrial processes. For example, in the process of making asphalt paving materials, sand and various grades of gravel or rocks—collectively referred to as virgin aggregate—are generally mixed with bituminous or liquid asphalt to form "hot mix" or HMA. However, the virgin aggregate must be sufficiently dry and hot or the liquid asphalt will not properly adhere to the sand and gravel. Also, the final product must be sufficiently hot such as 275-325 degrees Fahrenheit to be placed on the road bed. Therefore, in the typical operation, the virgin aggregate is introduced into one end of a large drum and heated by a burner before passing into a mixing zone where the liquid asphalt is introduced.

As is also known, it is desirable to know the initial moisture content of the virgin aggregate because that affects the number of BTUs required to dry and heat the virgin aggregate. If too little heat is applied, the virgin aggregate will not be sufficiently dried and heated; conversely, if too much heat is applied, energy is wasted and the virgin aggregate is overheated. Further, moisture content also effects the proper amount of liquid asphalt to be added because that is normally specified as ratio or percentage by weight of dry virgin aggregate (i.e. without water).

In a typical scenario, the sand, gravel, and rocks are stored in different piles or bins, and are loaded onto a common conveyor where they are mixed and fed into the large drum. Periodically, such as once or twice a day, an operator draws a sample of the virgin aggregate and carries it in a bucket to a lab where the moisture content is measured. Moisture content is generally defined as the ratio of water weight to the material weight plus the water weight. A conventional and very accurate method for determining moisture content is referred to as the water evaporation method. In such method, the sample of the virgin aggregate is first weighed, and then it is heated for a sufficient period of time to evaporate or drive off all of the moisture within the sample. Next, the sample is reweighed. The material weight plus water weight is, of course, provided by the initial weighing, and the water weight is the difference between the first weighing and the reweighing after the water has been driven off. It is noted that some states define moisture content as the ratio of water weight to dry material weight. In any event, the resulting moisture content value, typically expressed as a percentage, is then input to a control computer that makes automatic adjustments to the process. For example, if the moisture content is 5%, the computer might typically add to the heating requirements for dry aggregate an amount sufficient to drive off water weighing 5% of the total weight. Further, the computer might typically calculate that the virgin aggregate will weigh 5% less after the water has been driven off in the heating zone of the drum, and make a corresponding decrease in the liquid asphalt that is added.

The above described method has a number of disadvantages. First, it requires a substantial amount of operator time, and therefore is labor intensive and prone to errors. Further, the sampling rate is far too limited. The moisture contents of aggregate can change quickly and dramatically depending on atmospheric conditions, and the moisture content of the individual components generally change independently. Sand, for example, is very volatile in terms of moisture content; it will pick up moisture easily in a brief rain shower, but will also dry out more quickly than other materials with a little sunshine. Moisture content can also vary significantly depending on where a particular material is drawn from a stockpile. Also, another disadvantage is that it may be necessary to interrupt the flow of aggregate in order to obtain a sample.

An inaccurate initial moisture content value can also lead to another problem. In order to check for a specified ratio of liquid asphalt to virgin aggregate, an operator typically takes a sample of the finished hot-mix from the drum and carefully weighs it. Then he washes off all the liquid asphalt, dries the aggregate in an oven, and reweighs the sample. The difference between the beginning weight and the final weight is supposed to be the weight of the liquid asphalt. However, if all of the water wasn't driven off in the drum, it would be removed in this drying process, and recorded as liquid asphalt weight. This data could lead to the mistaken conclusion that the liquid asphalt content is too high, and result in an order to reduce the amount of liquid asphalt being added.

Another prior art method of determining moisture content of a material takes advantage of the fact that infrared energy is known to be absorbed by water at very specific wavelengths. That is, the absorptivity of infrared energy by water or moisture is known to be dependent on wavelength. In one commercially available system, the material is illuminated with broadband infrared energy. As is known, the reflected infrared energy power spectrum is altered according to the surface moisture on the material. For example, if the material has a relatively large amount of moisture on its surface, reflection of energy at wavelengths of high water absorption will be greatly reduced while reflections of energy at wavelengths of low absorption will be less affected by the surface moisture. It follows that if the material has relatively little water moisture, the reflected spectrum will be more uniform. In this system, a stationary light detector is positioned immediately behind a chopper wheel having a plurality of narrow band pass filters each disposed at a different angular orientation. Therefore, as the wheel rotates, the detector first sees infrared energy at wavelength $\lambda 1$ passing through a first filter, and subsequently sees infrared energy at wavelength $\lambda 2$ passing through a second filter. As a result, the detector provides a sequence of pulses having relative amplitudes that are a function of the absorption of infrared energy at the respective wavelengths by the surface moisture. In particular, one of the wavelengths $\lambda 1$ is not readily absorbed by surface moisture, and its pulses serve to provide a reference value related to surface parameters or characteristics of the material. The other wavelength $\lambda 2$ is more readily absorbed by surface moisture, and its pulses provide a measure of the surface moisture.

With the above described system, the operator initiates a calibration process wherein the ratio of pulses for λ1 and λ2 are stored. Then the operator takes a sample of the material and determines the moisture content of the sample by an accurate method such as the water evaporation method described above. The system has a keypad, and the operator inputs the actual moisture content for the stored ratio. The moisture content of the material can then be changed such as by wetting it with water, and then the process is repeated again building up a table of ratios and their corresponding moisture contents as actually measured. Subsequently, when the system is operating, the table is used to interpolate moisture contents for each real time ratio that is measured. In such manner, real time moisture content is electrically and automatically determined based on a correlation with previous measurements.

One problem with the heretofore described moisture sensing system is that it is relatively expensive. Further, during calibration in an industrial environment, the operator may have to carry the samples some distance to a lab to perform a water evaporation process. In addition to the labor time, trained operators are required, and errors may occur in transcribing moisture content data and entering it through the keypad of the sensor to create the table. Also, if the operational configuration of the materials changes, a complete and time consuming recalibration is generally required.

SUMMARY OF THE INVENTION

In accordance with the invention, a method for continuously producing signals representing moisture content of a material at a sensor station comprises the steps of activating the sensor station to produce calibration data corresponding to measurements of light at two different wavelengths reflected from the material, and transferring the calibration data to a portable or hand held computer. Next, the moisture content of a sample of the material is measured such as by a water evaporation process, and the measured moisture content is input to the hand held computer to create a table correlating data corresponding to measurements of light reflected at the two wavelengths to moisture content of the material. After transferring the table to the sensor station, the next step is continuously generating at the sensor station real time data corresponding to measurements of light at the two wavelengths reflected from the material, and using the table and the real time data to continuously produce signals representing moisture content. It is preferable that the calibration data comprise a ratio of measured light at one of the wavelengths to measured light at the other one of the wavelengths. It is also preferable that the measured light at each one of the wavelengths be normalized to ambient or background light. The method may also comprise a step of using real time data and interpolating between upper and lower moisture content values. Also, the sensor station activating step may comprise a step of directing broadband light on the sample and then rotating a chopper wheel with two selective band pass filters in front of a detector to produce a sequence of electrical pulses alternately corresponding to reflected light from the material at one of the two wavelengths.

With such arrangement, the sensor stations can be manufactured relatively inexpensively. In particular, the normal operator interface including a keypad and display can be eliminated, and in its place a connector can be used to transfer information to a portable or hand held computer such as a Micro-Wand. Therefore, a plurality of sensor stations can share the same hand held computer which is used to store the initial calibration data, and later create and transfer respective tables to the individual sensor stations. Further, because the transfer of calibration data to and tables from a hand held computer can be accomplished using relatively simple commands, a relatively inexperienced operator can be used to make the rounds and collect the samples; a more experienced operator who is less likely to make an error can be used back at a laboratory to create the tables. Also, a plurality of different tables can be stored for different materials, so it may not be necessary to go through a time consuming calibration process every time there is an operational change such as using a different material. An appropriate prestored table can be transferred or loaded into a sensor station from the hand held computer.

The invention may also be practiced by an industrial process system adapted for controlling the flow of a plurality of different materials on respective conveyors wherein the materials are transported to a region to form a composition of predetermined proportions of the materials by weight, the system comprising a plurality of sensor stations each disposed above a respective one of the conveyors wherein each sensor station comprises means for producing an electrical signal representing the real time moisture content of the respective one of the materials in response to measurement of reflected light at two different wavelengths from the respective one of materials. Also included is means responsive to the electrical signals for generating flow signals each corresponding to the flow rate of a respective one of the materials that compensates for moisture in the respective material to produce the predetermined proportion of materials by weight without moisture. The system further comprises means responsive to the flow rate signals for controlling the conveyors. In one embodiment, the flow rate signals are generated at the individual sensor stations, and in an alternate embodiment they are generated at a central computer or processor.

With such arrangement, an industrial process such as a "hot mix" process can be controlled, and individual materials of the virgin aggregate can be accurately controlled to predetermined proportions. For example, if the specification calls for proportions of 10% sand, 20% gravel grade 1, 30% gravel grade 2, and 40% rocks, this proportion can be very accurately provided because the moisture content of each one of the materials is provided on a real time basis. In response thereto, the flow rate of each one of the materials is individually adjusted to attain the desired proportion. Further, the moisture content of the virgin aggregate is known more accurately because the moisture contents of the individual component materials are known. Thus, in the case of a hot-mix process, the burner can be set to an optimum firing rate to drive off all the moisture and heat the aggregate to a predetermined temperature. Further, not too much firing is done so the aggregate is not overheated and fuel is not wasted. Further, the precise amount of liquid asphalt can be added because the dry weight of the virgin aggregate is accurately known on a real time basis.

BRIEF DESCRIPTION OF THE DRAWINGS

The foregoing objects and advantages will be more fully understood by reading the following Description of the Preferred Embodiment with reference to the drawings wherein.

DESCRIPTION OF THE PREFERRED EMBODIMENT

Figure 1:
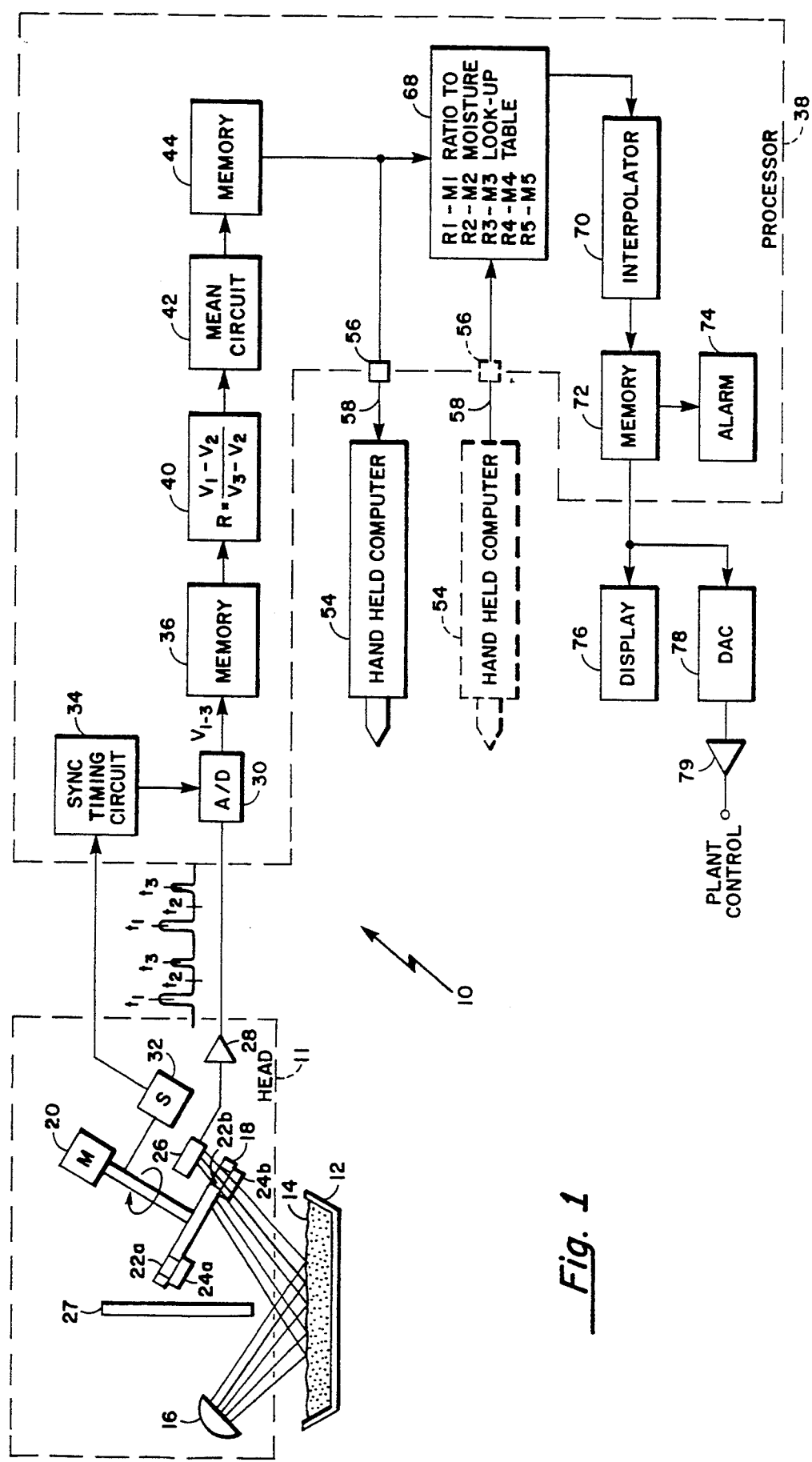
FIG. 1 is a simplified functional block diagram of a sensor station and its interface to a hand held computer.
Figure 3:
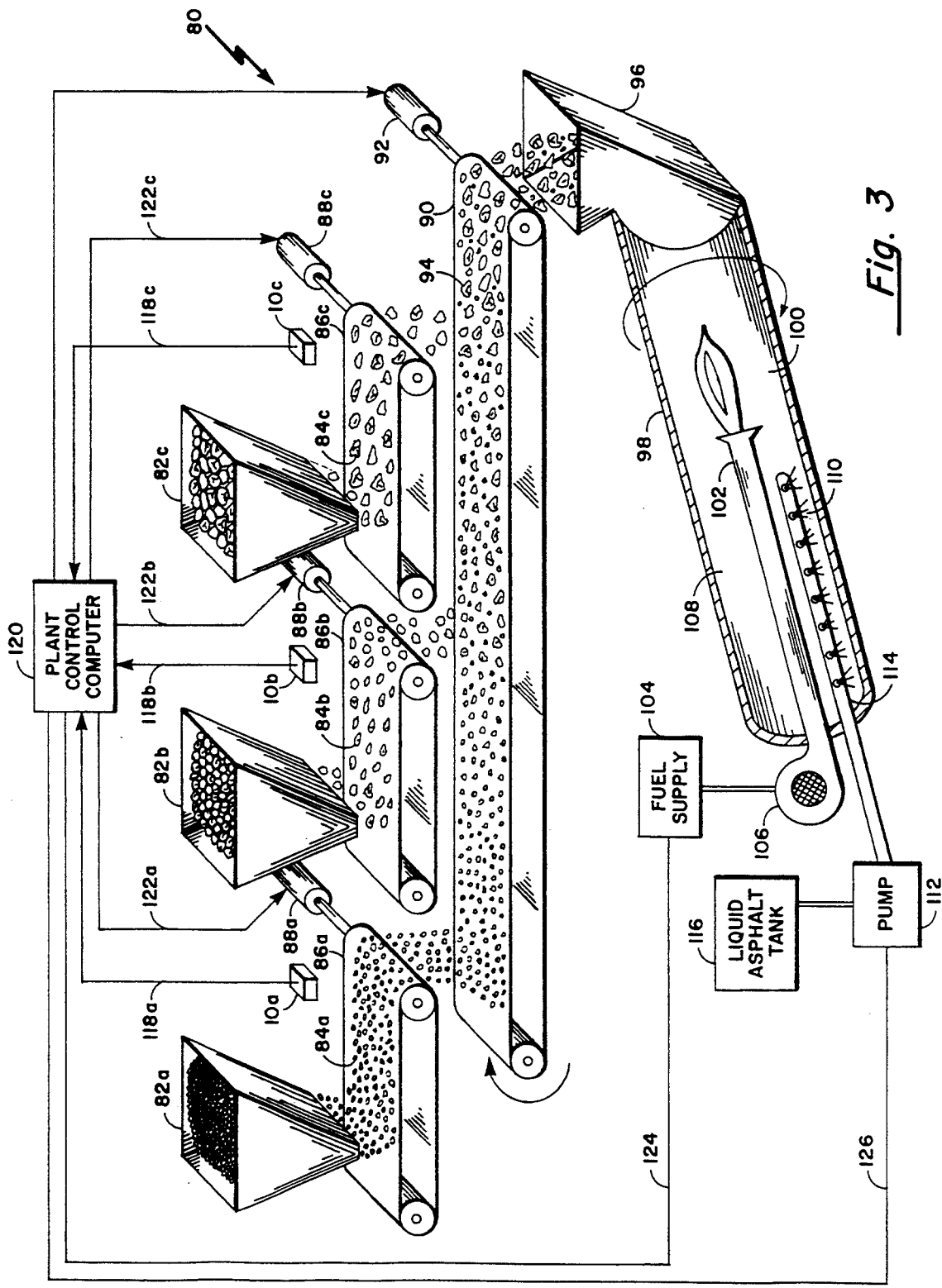
FIG. 3 shows an industrial system implementing a plurality of sensor stations.

Referring to FIG. 1, a sensor station 10 includes a sensor head 11 and a processor 38. Head 11 is disposed above a conveyor 12 that is carrying a material 14 such as sand, gravel or rocks which are the component materials of virgin aggregate 94 (FIG. 3). Although the apparatus and method described herein are with reference to making road paving materials, those skilled in the art will understand that the principles are applicable to many other industrial processes such as mixing materials for foods. Sensor head 11 includes a conventional source 16 of broad band light including infrared energy that is directed at an angle or off-axis from normal onto material 14, and a portion of the light is reflected upwardly towards off-axis disk 18 that is rotated at a suitable r.p.m. by motor 20. Disk 18 has two windows 22a and b at the same radius but different angular orientations, and each window 22a and b is covered by a respective narrow band pass filter 24a and b. Here, filter 24a passes a narrow band of infrared light centered at λ1 which may, for example be 1200 nanometers, and filter 24b passes a narrow band of infrared light centered at λ2 which may, for example be 1400 nanometers. Broad band light detector 26 is stationarily disposed within sensor head 11 above disk 18, and is aligned to receive light passing through filters 24a and b when they are properly aligned during rotation. A shield 27 is disposed between light source 16 and disk 18 to prevent a direct (i.e. nonreflecting) light path therebetween. Thus, for each revolution of disk 18, detector 26 sees reflected light at λ1 during a first time interval t1, reflected light at λ2 during a second time interval t3, and the remainder of the time sees background light. The output of detector 26 is coupled through signal conditioning amplifier 28 to analog to digital converter 30 which is part of processor 38. Thus, as shown, the input to analog to digital converter 30 is a periodic analog waveform of pulses t1 and t3 each corresponding to light reflecting from material 14 at respective wavelengths λ1 and λ2.

As is well known, light or infrared energy is absorbed by water at very specific wavelengths. In particular, infrared energy at a wavelength of 1400 nanometers is more readily absorbed than infrared energy at a wavelength of 1200 nanometers. Therefore, by using the reflected 1200 nanometer light as a reference value corresponding to the relative characteristics or parameters of the surface of the material 14, the reflected 1400 nanometer wavelength light provides a measure or is proportional to the water moisture on the surface of the material 14.

Conventional synchronizing device 32 provides a synchronizing signal to sync timing circuit 34. For example, synchronizing device 32 may be a mechanical device that provides a timing signal at one or more angular orientations of disk 18. Alternately, identifying reflector strips (not shown) can be disposed on the top of disk, and a light sensitive device can provide angular timing marks. In response to synchronizing signals, sync timing circuit 34 controls analog to digital converter 32 to cyclically sample the waveform from amplifier 28 at times t1, t2, and t3. As described above, the voltage at t1 corresponds to light reflected from material 14 at λ1, and the voltage at t3 corresponds to light reflected from material 14 at λ2. The voltage at t2 corresponds to background light when no window is disposed in front of detector 26.

The digital voltage values at times t1, t2, and t3, here identified as V1, V2, and V3, are stored in memory 36. Processor 38 then reads the values for V1, V2, and V3 from memory 36 and transfers them to math unit 40. Math unit 40 computes ratios of reflected infrared energy at λ1 and λ2. In particular, math unit 40 takes the values V1 and V3 for λ1 and λ2 at times t1 and t3, and normalizes each by subtracting the value V2 at time t2. Then, the ratio of these two differences is taken to provide ratio R which is the normalized ratio of reflected light at the two different wavelengths. Each normalized ratio is then transferred to mean or averaging circuit 42 where a plurality of ratios, such as a moving window of the last 25 ratios, are averaged and stored in memory 44.

Figure 2:
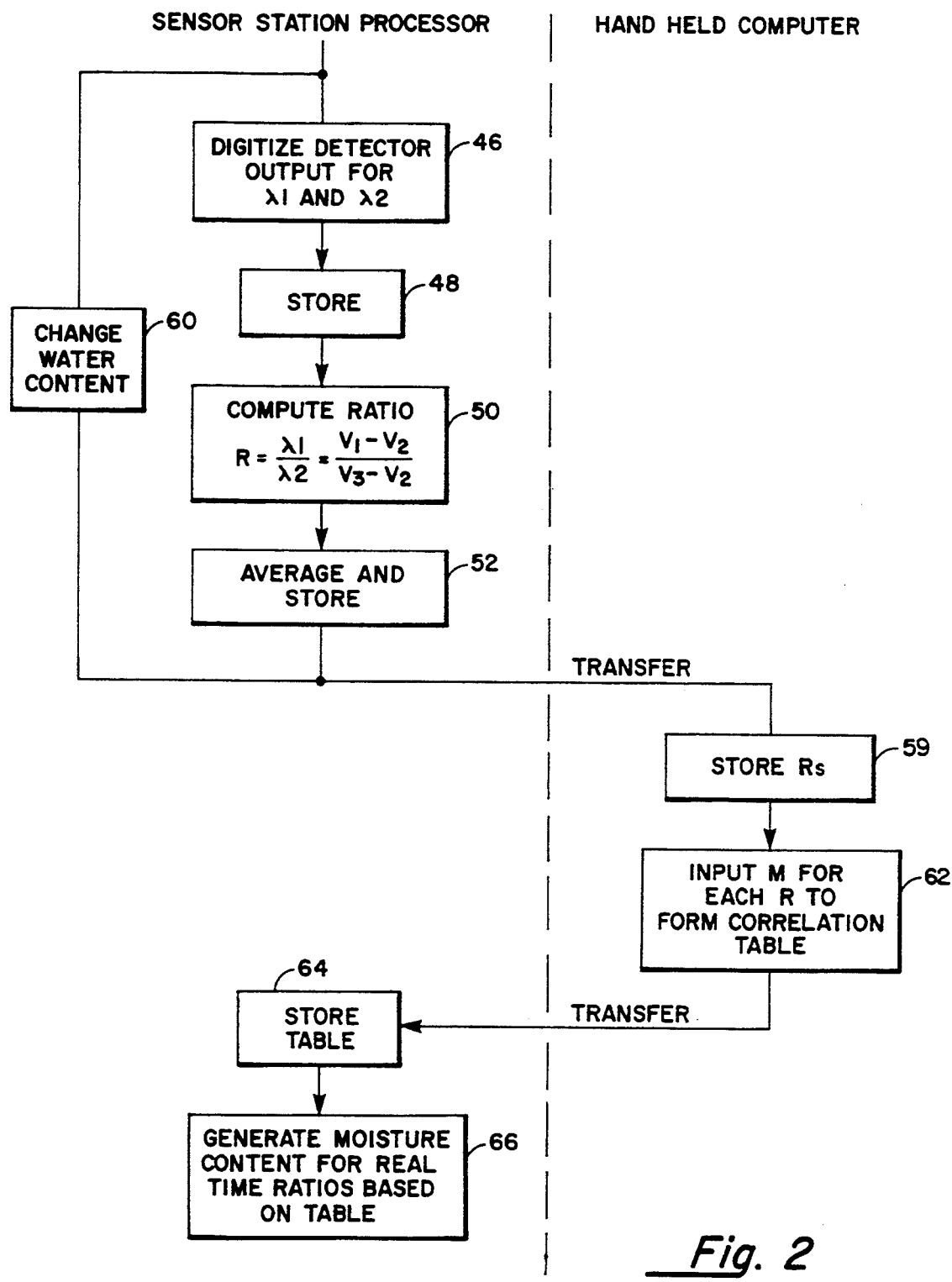
FIG. 2 is a flow diagram depicting calibration and operation of the sensor station using the hand held computer of FIG. 1.

Referring also to FIG. 2, a flow diagram of the operation of processor 38 is useful for describing a calibration procedure for sensor station 10. It is understood by those skilled in the art that it may be more practical and preferable to implement the functions of FIG. 1 using software, and the flow of FIG. 2 is described in that manner. As shown by block 46, processor 38 of sensor station 10 digitizes in analog to digital converter 30 the output of amplifier 28 for wavelengths λ1 and λ2, and also for time t2 when no window is aligned in front of detector 26. As shown by blocks 48 and 50, the values V1–V3 are stored and then ratio R is computed. As described above, it is preferable that the values be normalized. Next, in block 52, the ratios are averaged and stored. Still referring to FIG. 2 and also to FIG. 1, the averaged or mean ratio R is serially transferred to hand held computer 54 and stored as shown by block 59. One example of a hand held computer is a Micro-Wand III by Hand Held Products, Inc. of Charlotte N.C., which is widely used by overnight delivery services. As is well known, the Micro-Wand III has an optical reader, and also data can be transferred to and from the computer using a cable port. Here, hand held computer 54 is shown coupled to memory 44 through a connector 56 and cable 58. The programming of hand held computer 54 for transferring ratio data from memory 44 is well known to those skilled, and readily operated by operators with a minimum amount of instruction. The operator then takes a sample of material 14 and labels its container to correspond to the ratio R stored in hand held computer 54. As shown in block 60 of FIG. 2, the operator then changes the water content of material 14 such as by spraying it with water. The same procedure is followed to generate and transfer another ratio R to hand held computer 56, and take a corresponding sample of material 14. In the typical scenario, the operator transfers a plurality such as five ratios R1–5 to hand held computer 54, and for each takes a sample of material 14 at different conditions of wetness.

The operator next measures the moisture content of each sample using an accurate method such as a water evaporation process and, as shown in block 62, inputs to hand held computer 54 a moisture content value M1–5 for each R1–5 to form a correlation table. In particular, hand held computer 54 is programmed to provide a look-up table that gives a moisture content value M for each of the calibrated ratios R. With the table stored in hand held computer 54, and preferably a plurality of tables for different sensor stations 10 with different corresponding materials, the operator goes back to processor 38 of sensor station 10 and reconnects cable 58 to connector 56. Hand held computer 54 and connector 56 are shown dotted in FIG. 1 in this configuration. Then, as shown by block 64 of FIG. 2, the appropriate table is transferred and stored into sensor station 10. Referring to FIG. 1, the table correlating ratios R1-5 to moisture content values M1-5 is stored in memory 68.

Block 66 shows the next step is to generate moisture content values for real time ratios based on the table. In such generation, a real time or current ratio R is read from memory 44, and processor 38 uses the table in memory 68 to look up the corresponding moisture content. In the normal case where the real time ratio R is not exactly one of the ratios stored in the table, processor 38 uses interpolator 70 as shown in FIG. 1 to provide a more accurate moisture content value M. In particular, interpolator 70 selects the two ratio values from R1-5 that are closest to the real time ratio R, and interpolates the corresponding moisture content values M1-5 according to well known practice to obtain a more accurate real time moisture content value M.

The current or real time moisture content value M is stored in memory 72. Alarm 74 is responsive to the current or real time moisture content value M, and can be programmed to provide an audio or visual alarm if the moisture content value is beyond preset limits. The output of memory 72 is coupled to display 76 and digital to analog converter 78. Display 76, which provides an indication of the real time moisture content M of material 14 may be physically located at the site of sensor station 10, or remotely such as at a central computer. Alternately, hand held computer 54 may be used by the operator to read and display the real time moisture content M, thus eliminating the cost of a dedicated display at each sensor station 10. Digital to analog converter 78 converts the digital form stored in memory 72 to an analog voltage which is amplified in amplifier 79. An analog signal may be more adapted for use such as in a plant control method to be described.

Referring to FIG. 3, an industrial process system 80 is adapted for producing hot-mix for paving applications. A plurality of feed bins 82a-c are arranged to feed different materials 84a-c onto individual conveyors 86a-c. For example, in the production of hot-mix as here shown, bin 82a may typically store sand, bin 82b may typically store gravel of a predetermined grade or size, and bin 82c may typically store rocks of a predetermined size. Additional bins and materials may commonly be used. The bins 82a-c are typically filled by trucks or loaders from stockpiles. Even though the drivers may be instructed to load the driest materials into bins 82a-c, it can be assumed that each of the materials will have various amounts of water moisture. Conveyors 86a-c are independently driven by respective motors 88a-c. For purposes here, it is assumed that materials 84a-c are leveled on respective conveyors 86a-c so that the flow rate of a material 84a-c is dependent on the speed that the respective conveyor 86a-c as driven by the respective motor 88a-c. Other methods and devices could be used to alter the flow rates of materials 84a-c. As shown, conveyors 86a-c drop the respective materials 84a-c onto a common conveyor 90 driven by motor 92. As is known in the industry, the composite or composition of the respective materials 84a-c on conveyor 90 is commonly referred to as virgin aggregate 94.

In the typical operation, conveyor 90 is inclined to raise virgin aggregate 94 to a region from where it is fed or dropped into a chute 96 that feeds into drum 98. In conventional manner, the virgin aggregate 94 is first introduced into a drying zone 100 wherein it moves in counterflow to hot combustion gases produced by burner 102. In particular, fuel supply 104 delivers fuel to blower 106 where it is mixed with primary and later secondary combustion air before ignition at the output of burner 102. The burner 102 is disposed at a midpoint within drum 98, and the hot combustion gases flow towards and out the end where chute 96 is located. The motion of virgin aggregate 94 in the opposite direction is effected by gravity and the rotation of drum 98 with flighting (not shown) in conventional manner. As will be described in detail later herein, the firing rate of burner 102 is desirably sufficient to drive off all of the moisture from virgin aggregate 94, and raise its temperature to some predetermined level.

After being dried and heated in drying zone 100, the virgin aggregate 94 moves into mixing zone 108 where liquid asphalt 110 from pump 112 is pumped through perforated pipe 114. The spray of liquid asphalt 110 coats the virgin aggregate 94 to make hot-mix which is preferable at a temperature in the range 275-325 degrees Fahrenheit. The hot-mix is retrieved at the lower end of drum 98. The liquid asphalt is stored in liquid asphalt tank 116, and delivered to pump 112. Although not shown here, recycled asphalt materials could be delivered to mixing zone 108 in conventional manner.

As is well known, road paving materials such as hot-mix are generally required to meet certain specifications. For example, the specification may call for the virgin aggregate 94 to have dry weight proportions of 20:30:50, and the virgin aggregate 94 to liquid asphalt 110 to be 80:20. Prior art control computers have been programmed to compute the firing rate of burner 102 for drying and heating a predetermined weight of virgin aggregate 94, and to adjust or compensate that rate for a measured moisture content in the virgin aggregate 94. Further, such control computers have been programmed to deliver liquid asphalt 110 for a predetermined dry weight of virgin aggregate 94, and adjust or compensate the delivery rate for a measured moisture content in the virgin aggregate 94.

In accordance with the invention, the moisture contents of the individual materials 84a-c are accurately determined by a respective sensor station 10a-c located at each conveyor 86a-c. As described with reference to FIGS. 1 and 2, sensor station 10a provides a signal on line 118a that represents the moisture content of material 84a; sensor station 10b provides a signal on line 118b that represents the moisture content of material 84b; and sensor station 10c provides a signal on line 118c that represents the moisture content of material 84c. The signals on lines 118a-c may correspond to analog output signals from amplifier 79 of FIG. 1. Here, moisture content signals on lines 118a-c are fed to plant control computer 120. In response thereto, plant control computer 120 generates flow control signals which are fed to respective motors 88a-c to compensate for moisture content in respective materials 84a-c to produce a composite or composition of virgin aggregate 94 having a predetermined proportion. For example, flow rate signals may be calculated using the following formulas.

$$F1 = F_{20}(100/100-M1)$$

$$F2 = F_{30}(100/100-M2)$$

$$F3 = F_{50}(100/100-M3)$$

where F1-3 are the flow rate signals fed to motors $88a$–$c$ respectively. $F_{20}$ is a conventionally determined flow rate that will deliver the virgin aggregate 94 with 20% by weight of material $84a$ assuming the materials $84a$–$c$ are all dry. For illustration, that might be 20 tons per hour of sand. However, for this example, if material $84a$ had 10% moisture, then only 18 tons of material $84a$ would be delivered plus two tons of water. According to the formula, the flow rate for F1 would be increased by 100/100-M1 in order to compensate for the water moisture. Thus, material $84a$ would be delivered at a rate of 20 tons per hour, and there would also be approximately 2.2 tons of water delivered. Similarly, the flow rates of materials $84b$ and $c$ are adjusted to provide the 20:30:50 proportions of the example notwithstanding the fact that each may, and normally would, have an independent and variable moisture content. In an alternate embodiment, flow rate computations could be computed by the individual sensor stations $10a$–$c$ and fed directly to the respective motors $88a$–$c$.

Plant computer 120 also provides a control signal on line 124 to control the firing rate of burner 102. Here, line 124 is functionally shown connected to fuel supply 104. The firing rate is controlled by the following formula.

$$\text{Firing Rate} = F_C + F_M$$

where $F_C$ is the conventionally computed firing rate required to raise dry virgin aggregate 94 at the rate it is flowing to a predetermined temperature, and $F_M$ is the firing rate required to drive off the weight of water determined by multiplying the moisture content values times the respective flow rates of conveyors $86a$–$c$, and taking the sum.

Plant control computer 120 also provides a control signal on line 126 to pump 112 to determine the rate at which liquid asphalt is delivered into mixing zone 108. In particular, the rate at which virgin aggregate 94 flows into mixing zone 108 is readily and accurately known because the flow rates of materials $84a$–$c$ were increased as described above to provide the desired porportions, and the water is all driven off in the drying zone 100. Therefore, in this example, the delivery rate of liquid asphalt 110 is readily computed according to well known principles to provide the 80:20 ratio in this example.

With the above described arrangement and method, the moisture contents of the individual or component materials $84a$–$c$ are accurately measured on a real time basis, and the individual flow rates are adjusted or compensated to provide accurate proportions of the component materials $84a$–$c$ in the virgin aggregate 94. Further, because the moisture contents of the individual materials $84a$–$c$ are accurately known, the total moisture content of the virgin aggregate 94 is accurately known. Therefore, the firing rate of the burner 102 is regulated to optimize the heating and drying process. That is, enough heat is provided to drive off all the water, but energy is not wasted and the virgin aggregate 94 is not overheated. Further, because the weight of virgin aggregate 94 flowing into the mixing zone 108 is accurately known, the desired or specified ratio of virgin aggregate 94 to liquid asphalt 110 is accurately attained.

This concludes the description of the preferred embodiment. However, a reading of it by one skilled in the art will bring to mind many alterations and modifications that do not depart from the spirit and scope of the invention. For example, the principles could readily be applied to a system that also introduces recycled asphalt into drum 98. Therefore, it is intended that the scope of the invention be limited only by the appended claims.

What is claimed is:

1. A method for continuously producing signals representing moisture content of a material at a sensor station, comprising the steps of:

activating said sensor station to produce calibration data corresponding to measurements of light at two different wavelengths reflected from said material;

transferring said calibration data to a hand held computer;

measuring moisture content of a sample of said material;

inputting said measured moisture content of said sample into said hand held computer to create a table correlating data corresponding to measurements of light reflected at said two wavelengths reflected from said material to moisture content of said material;

transferring said table to said sensor station; and continuously generating at said sensor station real time data corresponding to measurements of light at said two wavelengths reflected from said material and using said table and said real time data to continuously produce signals representing moisture content.

2. The method recited in claim 1 wherein said calibration data comprises a ratio of measured light at one of said wavelengths to measured light at the other one of said wavelengths.

3. The method recited in claim 2 wherein said measured light at each one of said wavelengths is normalized to ambient light.

4. The method recited in claim 1 further comprising steps of activating said sensor station to produce a plurality of said calibration data measured at different wetness conditions of said material, measuring moisture content of a sample of said material at each of said wetness conditions, and creating said table from said plurality of calibration data and corresponding moisture content values.

5. The method recited in claim 1 wherein said signal producing step comprises a step of using real time data and interpolating between upper and lower moisture content values.

6. The method recited in claim 1 wherein said moisture content measuring step comprises a water evaporation process.

7. The method recited in claim 1 wherein said activating step comprises a step of said sensor station directing broadband light on said sample and then rotating a chopper wheel with two selective band pass filters in front of a detector to produce a sequence of electrical pulses alternately corresponding to reflected light from said material at one of said two wavelengths.

8. In a moisture content measuring system having a plurality of sensor stations each disposed to transmit light on a respective one of a plurality of different materials and measure light at two different wavelengths reflected from each of said respective materials, a method of calibrating and operating said sensor stations to produce a plurality of signals representing the moisture contents of the different materials comprising the steps of:

activating each one of said sensor stations to produce a plurality of calibration data each corresponding to a ratio of reflected light at said two different wavelengths measured for a respective one of a plurality of wetness conditions of the respective material;

transferring said plurality of calibration data from each of said sensor stations to a hand held computer;

measuring moisture content values of samples of said different materials at each one of said wetness conditions;

inputting said moisture content values of said plurality of samples of said different materials at said different wetness conditions into said hand held computer to create, for each of said materials, a table correlating ratios of measured reflected light at said two wavelengths to corresponding moisture content values;

transferring from said hand held computer to each of said sensor stations a table corresponding to the material at said sensor station; and continuously generating at said sensor stations real time data corresponding to ratios of measured light at said two wavelengths reflected from the respective material, and using said respective table and said real time data to produce at each one of said sensor stations electrical signals representing the real time moisture content of the respective material.

9. The method recited in claim 8 further comprising the step of normalizing the measured light at said two wavelengths to background light before forming said ratios.

10. The method recited in claim 8 wherein said signal producing step comprises a step of using real time data and interpolating between upper and lower moisture content values.

11. The method recited in claim 8 wherein said moisture content measuring step comprises a water evaporation process.

12. The method recited in claim 8 wherein said activating step comprises a step of said sensor station directing broadband light on said sample and then rotating a chopper wheel with two selective band pass filters in front of a detector to produce a sequence of electrical pulses alternately corresponding to reflected light from said material at one of said two wavelengths.

13. The method recited in claim 8 further comprising the step of moving said materials on respective conveyors and each of said sensor stations is disposed above a respective one of said conveyors.

14. The method recited in claim 8 further comprising the step of directing said materials on said conveyors to a common region to form a composition of said respective materials.

15. The method recited in claim 14 further comprising the step of controlling the flow rate of said materials on said conveyors in response to said electrical signals representing the real time moisture contents of said materials to form a composition of predetermined proportions by weight without moisture.

16. The method recited in claim 15 wherein said flow rate controlling step comprises the steps of computing the flow rate of said material in a dry condition to provide said predetermined proportion and then adjusting said rate upwardly to compensate for part of the weight on the conveyor being moisture.

17. A sensor station adapted for disposition above a material of unknown moisture content, comprising:

means for measuring light at two different wavelengths reflected from said material;

means for providing a ratio corresponding to the reflected light measured at said two wavelengths;

means for transferring a plurality of said ratios measured at different wetness conditions of said material to a hand held computer;

means for receiving from said hand held computer and storing a table correlating ratios of said measured light at said two wavelengths to moisture content of said material; and means responsive to a real time measured ratio and said table for producing a signal representing the real time moisture content of said material.

* * * * *